United States Patent
Brown

(10) Patent No.: US 8,795,697 B2
(45) Date of Patent: Aug. 5, 2014

(54) SANITIZING COMPOSITION AND METHOD OF PREPARATION

(76) Inventor: James S. Brown, Gilbert, AZ (US)

( * ) Notice: Subject to any disclaimer, the term of this patent is extended or adjusted under 35 U.S.C. 154(b) by 1826 days.

(21) Appl. No.: 11/102,017

(22) Filed: Apr. 9, 2005

(65) Prior Publication Data

US 2005/0271595 A1 Dec. 8, 2005

(30) Foreign Application Priority Data

Jun. 3, 2004 (GB) .................. 0412329.5

(51) Int. Cl.
*A01N 25/02* (2006.01)
*A61K 8/00* (2006.01)

(52) U.S. Cl.
USPC ........... 424/405; 424/401; 424/404; 424/420; 510/130; 510/138; 510/139; 510/158

(58) Field of Classification Search
USPC .......... 424/401, 404, 405; 510/130, 138, 139, 510/158
See application file for complete search history.

(56) References Cited

U.S. PATENT DOCUMENTS

| 5,089,269 A * | 2/1992 | Noda et al. .................. 424/456 |
| 5,476,660 A * | 12/1995 | Somasundaran et al. ..... 424/401 |
| 5,900,067 A | 5/1999 | Jones |
| 5,968,530 A * | 10/1999 | Arquette ...................... 424/401 |
| 6,010,991 A | 1/2000 | Dabestani |
| 6,045,813 A * | 4/2000 | Ferguson et al. ............. 424/401 |
| 6,228,385 B1 | 5/2001 | Shick |
| 6,319,507 B1 * | 11/2001 | Delrieu et al. ................ 424/401 |
| 6,376,438 B1 | 4/2002 | Rosenberger et al. ........ 510/139 |
| 6,432,421 B1 * | 8/2002 | Brown et al. ................. 424/401 |
| 6,432,428 B1 * | 8/2002 | Arquette et al. ............. 424/401 |
| RE38,141 E | 6/2003 | Brown et al. |
| 6,617,294 B2 | 9/2003 | Narula et al. |
| 6,727,210 B1 | 4/2004 | Perdew, Jr. |
| 7,306,809 B2 * | 12/2007 | Sojka et al. .................. 424/401 |
| 2003/0197122 A1 | 10/2003 | Faiola et al. |
| 2004/0265343 A1 * | 12/2004 | Hill .............................. 424/400 |

FOREIGN PATENT DOCUMENTS

| CH | 690665 | 12/2000 |
| CH | 690665 A5 | 12/2000 |
| GB | 1468295 A | 3/1977 |
| RU | 2044036 C1 | 9/1995 |
| WO | 99/43205 A | 9/1999 |
| WO | 99/47105 A2 | 9/1999 |
| WO | 2005/004831 A1 | 1/2005 |
| WO | WO2008118143 | 10/2008 |

OTHER PUBLICATIONS

UK Intellectual Property Office, Office action on corresponding GB patent application # GB0412329.5.
EP 05 85 6772 Supplementary European Search Report dated Oct. 6, 2010.

* cited by examiner

*Primary Examiner* — Gina C Justice
(74) *Attorney, Agent, or Firm* — Hahn Loeser & Parks LLP

(57) ABSTRACT

The invention provides a sanitizing composition in the form of a viscous liquid or gel suitable for use as a handwash composition comprising alcohol, water and a thickener wherein the viscous liquid or gel has particles suspended therein, wherein said particles provide the composition with a granular texture and are capable of being worn away when rubbed. The particles may deliver one or more agents to the skin e.g. antimicrobial, antibacterial or antiviral agents, emollients and/or moisturizers, fragrances, colorings or UV markers.

18 Claims, No Drawings

SANITIZING COMPOSITION AND METHOD OF PREPARATION

This application is a continuation of pending Great Britain patent application serial No. 04 12329.5 filed on Jun. 3, 2004.

FIELD OF THE INVENTION

This invention relates to a sanitizing composition and its method of preparation. More particularly, but not exclusively, the invention relates to an alcohol hand sanitizer for use in a health care environment.

BACKGROUND OF THE INVENTION

Currently, hospital acquired infections affect about 100,000 Britons each year and generate costs of £bn. An increasing percentage of these infections are resistant to antibiotics. The hospital "superbug", methicillin resistant *Staphylococcus aureus* (MRSA), kills between 5,000 and 20,000 Britons each year. Other multiple-resistant pathogens such as vancomycin resistant Enterococci (VRE), vancomycin intermediate *Staphylococcus aureus* (VISA) have been observed in the UK. As pervasive use of antibiotics continues, more multiple-resistant pathogens are expected to appear in the future. This trend has increased over the past 10 years.

Health care environments are the prime breeding grounds for multiple-resistant pathogens due to the high ambient levels of antibiotics, the density of human hosts with weakened immune systems, and the ready means of cross-inoculation afforded by health care workers tending to many different patients. The single most significant inoculation vector is the health care worker's hand.

Hand hygiene is of primary importance in controlling infection in a health care environment. There exist specific standards to specify when, where and how health care workers (HCW) should clean their hands. In the U.K., the National Health Service (NHS) is challenged to enforce these standards to the point at which infection rates decrease. Enforcing these, or any future updated standards of hygiene will be crucial in controlling hospital infection. Unfortunately, many HCW fail to clean their hands properly thereby aiding the cross-inoculation of germs to many different patients. HCW line management cannot rely on conventional shaming methods to overcome HCW baseline reluctance to wash their hands.

Many of the problems associated with the failure to prevent cross-inoculation can be linked with HCW negative feelings towards hand washing using conventional methods. The traditional form of hand washing using soap and water is considered by many HCW as time consuming. HCW are becoming increasingly busy, and may not find enough time to carry out the important process of washing often enough. Sinks are not always located in the most convenient places; HCW may have to go to great lengths to find a sink to wash their hands, and may not do so if it is too inconvenient. Constant washing with soap can also cause skin irritation and dryness. All these factors contribute to the need to make handwashing more attractive and convenient to the HCW in order to improve health hygiene standards.

Alcohol hand sanitizers (AHS) have been introduced into health care environments to provide a solution to this problem. Currently, the use of alcohol solutions, gels and foams are established hospital practise. They are considered more effective than soap in reducing the number germs on hands. The proportion of alcohol contained within the alcohol gel formulations can vary between 60 and 95%. They are used extensively to sanitize hands because of their ability to denature proteins. Alcohol has an excellent initial antimicrobial log reduction activity of gram-postive and gram-negative bacteria, fungi and multi-drug resistant pathogens such as Vancomycin-resistent *Enterococcus* (VRE) and methicillin-resistent *Staphylococcus aureus* (MRSA).

AHS exhibit many advantages over soap and water. AHS can be used at any time and anywhere without water or towels. Hand washing using AHS is achievable if soap and water are not readily available. AHS can be provided in different types and sizes of bottles, bowls by the patient's bed or in already existing dispensers, unlike traditional methods where the HCW needs to locate a sink nearby. AHS are more accessible and convenient than the traditional soap and water method. Another advantage is that AHS take less time to use and the high volatility of alcohol means that they dry on the hands quickly.

Extra antimicrobial agents have been dissolved into the alcohol of known AHS formulations to give greater efficacy against bacterial, viral and fungal pathogens than simple AHS formulations. This is taught by U.S. Pat. No. 6,248,343 to Jampani et al, and U.S. Pat. No. 6,022,551, also to Jampani et al.

Conventional AHS, even those that include extra antimicrobial agents, do not have the residual ability to inhibit microorganisms over the whole day. When the alcohol has evaporated to leave the hands dry, there is very little antimicrobial agent and even less residual alcohol for the AHS to have a continuing disinfecting effect on the hands. Therefore it is necessary for the HCWs to wash their hands regularly, before and after each patient.

Constant use of AHS can cause unpleasant irritation and dryness of the skin. Some AHS have added emollients and moisturisers to the formulation to combat the dehydrating effect that alcohol has on skin. An emollient is a product that makes dry or sore skin softer or less painful and a moisturiser is a product for application to skin to stop it from becoming dry. Many products provide both emollient and moisturizing properties.

U.S. Pat. No. 4,956,175 to Lee teaches the use of high alcohol content antimicrobial gel compositions for disinfecting hands possessing moisturising and conditioning agents, and U.S. Pat. No. 6,617,294 to Narula et al. describes a waterless sanitizing hand cleanser comprising an effective amount of alcohol to produce a reduction in micro organisms on the surface of the skin, and emollients or oils for skin moisturising. In the above patents, the moisturiser is simply added to the alcoholic base formulation to tackle it's dehydrating effects.

As well as emollients and moisturisers, other AHS formulations add extra ingredients such as fragrance and colourings to make them more attractive and aesthetically pleasing. The use of fragrance and colour in the AHS formulation is a matter of personal preference and does not necessarily make it more attractive to the HCW. Some HCW have complained about the AHS leaving a coloured residue on their hands and clothing. The added ingredients may also cause allergic reactions.

The adverse side effects mentioned above lead to a lack of acceptance of the AHS and may result in HCW not washing their hands often enough nor for long enough. If this is the case, the AHS will not work to its maximum ability and prevent the spread of infections. There is a need for a better, more effective method of enforcement of hand hygiene standards.

In one embodiment, the present invention provides a novel antimicrobial AHS that facilitates the enforcement of proper hand hygiene standards by incorporating particles in the alcohol formulation. The suspended particles are sufficiently hard have a gritty feeling and disappear only after a standard and controllable amount of rubbing energy has been expended. For this reason, a HCW is compelled to give the alcohol gel a more thorough and complete application than a conventional AHS.

By appropriate choice of particle, the antimicrobial AHS can be designed to be compatible with HCW skin and can take into account the personal preferences of the HCW. For example, the particles may contain an emollient and/or moisturiser. These changes to the AHS will make it more attractive to the HCW and should result in the formulation being used more regularly. All the active ingredients can be provided in the AHS contained in hard, suspended particles. The AHS particles can be modified to combat bacteria, bacterial spores, viruses', and fungus/yeast, specific to the requirements of the health care environment at the time. If desired, the suspended particles can be seen and distinguished visually; therefore it is possible to identify the ingredients and check the compatibility of the AHS with the HCW and the health care environment. A fragrance or UV-activated particles may also be incorporated within the AHS. This would allow the HCW supervisor to check whether the HCW is adhering to the hand sanitation regulations by smell or by shining UV light onto hands. The flexibility and visuality of the formulation will increase its acceptance by HCW.

It is known to incorporate emollients in their "dry form" as soft suspended particles or beads in cosmetic, personal care and pharmaceutical products as illustrated in U.S. Pat. No. RE38,141E to Brown and U.S. Pat. No. 5,968,530 to Arquette. U.S. Pat. No. 6,432,421 to Brown et al. provides details regarding emollient compositions with polyethylene beads. These products are alcohol-free or contain low amounts of alcohol. In contrast, the composition of the invention contains a high amount of alcohol. Further, the prior art provides no guidance to solve the problem of enforcing hand hygiene standards.

BRIEF SUMMARY OF THE INVENTION

The present invention seeks to provide a sanitizing composition for the enforcement of hand hygiene standards, so as to overcome, or at least reduce the above-mentioned problems of the prior art.

Accordingly, in a first aspect the invention provides a sanitizing composition in the form of a viscous liquid or gel suitable for use as a handwash composition comprising alcohol, water and a thickener wherein the viscous liquid or gel has particles suspended therein wherein said particles provide the composition with a granular texture and are capable of being worn away when rubbed.

In another aspect the invention provides a method of preparing a sanitizing composition suitable for use as a handwash composition said method comprising the steps of:

mixing together an alcohol, water and a thickener to form a viscous liquid or gel;

adding particles to the viscous liquid or gel to provide the composition with a granular texture, said particles being capable of being worn away when rubbed; and, mixing the particles and the viscous liquid or gel to suspend the particles substantially uniformly in the viscous liquid or gel.

DETAILED DESCRIPTION OF THE INVENTION

The major component of the proposed sanitizing composition is alcohol. It is useful as an agent for the immediate disinfection of topical surfaces e.g. the hands of HCW. Alcohol is well known to dehydrate the skin and the larger the proportion of alcohol, the greater the dehydrating effects. A solution made of pure alcohol would be very dehydrating and damaging to the skin if used regularly to wash hands. The quantity of alcohol contained within the composition may vary from 30 to 95% by weight. More preferably the quantity of alcohol is from 45 to 90% by weight, and most preferably within the range of 55 to 80% by weight, e.g. 62% by weight.

Preferably, the alcohol is selected from the group comprising ethanol, isopropanol, n-propanol, n-butanol, 2-butanol, isobutanol, 2-isobutanol, benzyl-alcohol or a mixture thereof. Ethanol or isopropanol is most preferred.

The composition of the invention contains water as water boosts the efficacy of the alcohol as a disinfectant. However, a solution created from solely water and alcohol has such a low viscosity that a HCW would find it troublesome to wash their hands. The fluid would pour very quickly out of a dispenser for the fluid onto the hands to be cleaned and would easily run off the hands onto the surrounding surfaces. As it is quite difficult to control the flow of a very thin fluid, it is likely that more fluid than needed would be used. A fluid having a thicker consistency would be easier to dispense, manipulate and rub into hands. For this reason, the composition of the invention contains a thickener for increasing the viscosity of the alcohol/water solution.

The quantity of thickener may vary from 0.05 to 10% by weight depending on the specific ingredient chosen. However, the concentration of thickener is best described in terms of the achieved viscosity at 25° C.

The thickener may be employed in an amount such that the composition has a viscosity from 100 to 100,000 cP at 25° C., preferably from 5,000 to 50,000 cP at 25° C. and most preferably from 10,000 to 20,000 cP at 25° C.

Examples of suitable thickners include Acrylates/C1O-C30 alkyl acrylate crosspolymer, Acrylates/ceteth-20 itaconate copolymer, Acrylates/ceteth-20 methacrylates copolymer, Acrylates/palmeth-25 acrylate copolymer, Acrylates/steareth-20 itaconate copolymer, Acrylates/steareth-20 methacrylate copolymer, Acrylates/steareth-50 acrylate copolymer, Acrylates NA crosspolymer, Acrylates/vinyl isodecanoate crosspolymer, Acrylic acid/acrylonitrogens copolymer, Algin, Aluminum/magnesium hydroxide stearate, Ammonium acrylates/acrylonitrogens copolymer, Ammonium alginate, Ammonium polyacryl dimethyl tauramide NA, Arachidyl alcohol, Attapulgite, Behenic acid, Behenyl alcohol, Behenyl behenate, Bentonite, CI-5 alkyl galactomannan CIS-36 acid, CIS-36 acid glycol ester, CIS-36 acid triglyceride, Calcium alginate, Calcium carrageenan, C 12-15 alcohols, C12-16 alcohols, Caprylic alcohol, Carbomer, Carboxymethyl hydroxyethylcellulose, Carrageenan (*Chondrus crispus*), Cellulose, Cellulose gum, Ceteareth-3, Ceteareth-60 myristyl glycol, Cetearyl alcohol, Cetearyl behenate, Cetearyl octanoate, Cetearyl stearate, Cetostearyl stearate, Cetyl alcohol, Cetyl betaine, Cetyl esters, Cetyl hydroxyethylcellulose, Cetyl myristate, Cetyl palmitate, Cocamide, Cocamide DEA, Cocamide MEA, Cocamide MIPA, Cocamidopropylamine oxide, Cocamidopropyl betaine, Coco betaine, Coco/oleamidopropyl betaine, Coco-rapeseedate, Cocoyl amido hydroxy sulfobetaine, Cocoyl monoethanolamine ethoxylate, Colloidal silica sols, DEA-hydrolyzed lecithin DEA-linoleate, DEA-oleth-3 phosphate, DEA oleth-10 phosphate, Decyl alcohol, Dextran, Dextrin, Dihydroxyethyl Tallowamime, Dioleate, Dilaureth-10 phosphate, Dilinoleamidopropyl dimethyl amine, Dioleth-S phosphate, DMHF, Ethoxylated fatty alcohol, Ethylcellulose, Gellan gum, Glucouis, Glyceryl behenate, Glyceryl poly methacrylate, Glyceryl stearate, Glyceryl stearate SE, Guar (*Cyanopsis tetragonoloba*) gum, Guar hydroxypropyltrimonium chloride, Hectorite, Hexyl alcohol, Hydrated silica, Hydrogenated rapeseed oil, Hydrogenated starch hydrolysate, Hydrogenated vegetable glycerides, Hydrolyzed oat flour, Hydrolyzed transgenic collagen, Hydroxyethylcellulose, Hydroxypropylcellulose, Hydroxypropyl chitosan, Hydroxypropyl guar, Hydroxypropyl methylcellulose, Isoceteth-10, Isostearamide DEA, Isostearamidopropylamine oxide, Jojoba wax, Karaya (*Stericulia urens*) gum, Lauramide DEA, Lauramidopropyl betaine, Laureth-3, Laureth-10, Lauric acid, Lauric-linoleic DEA, Lauroyl-linoleoyl diethanolamide, Lauroyl-myristoyl diethanolamide, Lauryl alcohol, Lauryl betaine, Linoleamide DEA, Linoleic acid, Linolenic acid, Lithium magnesium sodium silicate, Locust bean (*Ceratonia siliqua*) gum, Mannan gum, Magnesium aluminum silicate, MDM hydantoin, Methylcellulose, Montmorillonite, Myristamide DEA, Myristamide MEA, Myristamine oxide, Myristic acid, Myristyl alcohol, Octacosanyl stearate, Oleamide, Oleamide DEA, Palmitamide MEA, Paraffin, Pectin, PEG-8, PEG-80 Glyceryl tallowate, PEG-8 PPG-3 Diisostearate, PEG-200 Hydrogenated glyceryl palmate, PEG-5M, PEG-9M, PEG-23M, PEG-45M, PEG-90M, PEG-160M, PEG-6 beeswax, PEG-S beeswax, PEG-12 beeswax, PEG-150/decyl/SMDI copolymer, PEG-4 diisostearate, PEG-8 dioleate, PEG-3 distearate, PEG-4 distearate, PEG-8 distearate, PEG-150 distearate, PEG-18 glyceryl oleatelcocoate, PEG-200 glyceryl stearate, PEG-28 glyceryl tallowate, PEG-200 glyceryl tallowate, PEG-7 hydrogenated castor oil, PEG-40 jojoba oil, PEG-3 lauramide, PEG-3 laura mine oxide, PEG-2 laurate, PEG-120 methyl glucose dioleate, PEG-4 oleamide, PEG-ISO pentaerythrityl tetrastearate, PEG-55 propylene glycol oleate, PEG-4 rapeseedamine, PEG-160 sorbitan triisostearate, PEG-S stearate, PEG-75 stearate, PEG-100 stearate, PEG-150/stearyl/SMDI copolymer, PEG-50 tallow amide, Pentaerythrityl tetrabehenate, Pentaerythrityl tetrastearate, Poloxamer 105, Poloxamer 124, Poloxamer 185, Poloxamer 237, Poloxamer 238, Poloxamer 338, Poloxamer 407, Polyacrylic acid, Polyquarternium-37, Polysorbate 20, Potassium alginate, Potassium chloride, Potassium oleate, Potassium stearate, PPG-5-ceteth-10 phosphate, PPG-14 laureth-60 alkyl dicarbamate, PPG-14 palmeth-60 alkyl dicarbamate, Propylene glycol stearate, Propylene glycol stearate SE, PVMIMA decadiene crosspolymer, PVP, Quaternium-90, Bentonite, Quatemium-18 bentonite, Quaternium-18 hectorite, Rapeseed oil, ethoxylated high erucic acid, Ricinoleamide MEA, Sclerotium gum, Sesamide, DEA, Silica, Sodium acrylates/vinyl isodecanoate crosspolymer, Sodium carbomer, Sodium carrageenan, Sodium ceteth-13-carboxylate, Sodium chloride, Sodium hyaluronate, Sodium hydroxypropyl starch phosphate, Sodium isostearoamphopropionate, Sodium lauryl sulfoacetate, Sodium magnesium silicate, Sodium stearate, Sorbitan sesquiisostearate, Sorbitan tristearate, Soy amide DEA, Soyamidopropyl betaine, Starch polyacrylonitrile copolymer—potassium salt, Starch polyacrylonitrile copolymer—sodium salt, Stearalkonium bentonite, Stearalkonium hectorite, Stearamide, Stearamide, DEA, Stearamide MEA, Stearamide MEA-stearate, Stearamidopropyl dimethyl amine lactate, Stearamine oxide, Steareth-10 alkyl ether/acrylates copolymer, Stearic acid, Stearyl alcohol, Synthetic beeswax, Tallowamide MEA, TEA-acrylates/acrylonitrogens copolymer, Tragacanth (*Astragalus gummifer*) gum, Tribehenin, Trideceth-2 carboxamide MEA, Trihydroxystearin, Tromethamine magnesium aluminum silicate, Wheat germamide DEA, Wheat germamidopropyl betaine, Xanthan gum, and mixtures thereof As understood in the art, some thickeners need to be mixed with an activating agent to induce the thickener to form a viscous gel.

Preferably, the thickener is chosen to provide the water/alcohol solution with a clarity from 70% to 100%.

The term "water/alcohol solution" is used interchangeably with "water/alcohol fluid" and "water/alcohol gel" within this description. These terms refer to a mixture of the alcohol, water and thickener to produce a fundamental alcohol sanitizer formulation, which is the basis from which all embodiments of this invention are created.

Unlike other AHS preparations, the composition of the invention includes suspended particles that can be worn away when rubbed. The particles need to be sufficiently hard so that the HCW can feel them on their skin and feel compelled to rub their hands until they are completely gone, although not so hard that they are abrasive or uncomfortable to the skin.

Preferably, the suspended particles are of a size, hardness and uniformity, so that when the composition is rubbed into the skin, the suspended particles are worn away until they can no longer be felt against the skin. The particles can be made to 'disappear' after a controllable amount of rubbing energy has been expended. For this reason, HCW are compelled to give the composition a more thorough and complete application than a conventional AHS. The presence of the particles enforces a more thorough application of the composition thereby facilitating the enforcement of proper hand hygiene standards in the health care environment.

The hardness of the material from which the particles are made can be measured using a penetrometer in accordance with the standard test method ASTM D 1321-92. Preferably, the particles are formed of a composition having a penetration from 50 to 200, more preferably from 80 to 160 as measured in accordance with ASTM D 1321-92 at 25° C.

The longest dimension of these particles e.g. diameter may range from 100 µm to 2000 µm, preferably from 250 µm to 1500 µm. The particles are chosen to be toxicologically safe to the HCW and substantially insoluble in the composition so that the particles do not undesirably bleed into the alcohol/water fluid in which they are suspended.

In deciding on the size and hardness of the particles to be used for enforcing hand hygiene standards, the particles should desirably have a measured and constant resistance to being abraded as they are rubbed into the skin. The resistance is determined by both the physical size of the particle and its chemical structure. For any given particle, the energy required to fully abrade the particle is proportional to its size. Also, for particles of the same size, the energy required to fully abrade a particle is proportional to its hardness. Hence, appropriate particles may be chosen according to various combinations of size and hardness. For example, a particle having a diameter of about 100 µm and a hardness of about 120 as measured above is particularly suitable.

Preferably, the particles are formed of a composition that will spread and be absorbed into the skin.

The particles may be formed of a composition comprising one or more hydrocarbons, fatty alcohols, fatty acids and esters thereof, agar, starches, silicon-based compounds e.g. silicates and natural or synthetic polymers e.g. gelatins.

Preferably, the particles are substantially homogeneous.

The particles may have various shapes and sizes. Spherical particles are preferred.

Examples of suitable particles include Florasomes® (monosized soft spheres of jojoba esters), thalaspheres (collagen) and liposheres (polymers derived from animal, vegetable or synthetic sources e.g. alginate, agar and gelatin).

The concentration of the particles in the composition may vary from 0.01% to 10% by weight e.g. from 0.1% to 10% by weight, preferably from 0.1 to 5% by weight, more preferably from 0.5 to 2% by weight.

These particles may deliver one or a combination of agents directly to the skin e.g. antimicrobial agents, emollients and/or moisturisers, fragrances, colourings and UV markers. Preferably, the agent(s) is (are) substantially uniformly distributed throughout the particle. The specific combination of these agents present in the alcohol/water fluid will have a direct influence on the concentration of the particles in solution. These attributes play a decisive role in achieving improved hand hygiene in a health care environment.

Preferably, at least some of the particles contain an emollient and/or moisturizer. The incorporation of one or more agents that soften and soothe the skin and provide moisturization within the alcohol/water gel helps to overcome skin irritation, dermatitis and dry skin objections that HCW have against traditional washing methods.

Suitable emollients and/or moisturizers include Acetamidopropyl trimonium chloride, Adenosine triphosphate, Aesculus chinensis extract, Algae (*Ascophyllum nodosum*) extract, Algae (*Codium tomentosum*) extract, Algae extract, *Aloe barbadensis*, *Aloe barbadensis* gel, *Aloe barbadensis* extract, *Aloe barbadensis* leaf juice, *Aloe capensis* extract, *Aloe vera* oil, Aluminum starch octenylsuccinate, Ammonium-S-lactate, Amniotic fluid, Apple (*Pyrus malus*) extract, Apricot (*Prunus armeniaca*) kernel oil, Arginine PCA, *Artemisia apiacea* extract, *Astrocaryum murumuru* extract, Atelocollagen, Avocado (*Persea gratissima*) extract, Avocado (*Persea gratissima*) oil unsaponifiables, Avocado (*Persea gratissima*) oil, Avocado sterols, Babassu (*Orbignya oleifera*) oil, Bactris gasipaes extract, Balsam copaiba (*Copaifera officinalis*), Benincasa hispids extract, Betaine, Biosaccharide gum-I, Bis-diglyceryl polyacyladipate-2, Black currant (*Ribes nigrum*) extract, Black currant (*Ribes nigrum*) oil, Borage (*Borago officinalis*) seed oil, Brazil nut (*Bertholetta excelsa*) oil, Brazil (*Bertholetta excelsa*) nut extract, Butadiene/Isoprene copolymer, Butylglucoside caprate, Calcium pantothenate, Calcium protein complex, Camellia japonica oil, *Cannabis sativa* oil, Canola oil, Canola oil unsaponifiables, Capryl glycol, Caprylic/capric glycerides, Caprylic/capric/lauric triglyceride, Caprylic/capric/linoleic triglyceride, Caprylic/capric/oleic triglycerides, Caprylic/capric triglyceride, Cashew (*Anacardium occidentale*) nut oil, C10-30 cholesterol/lanosterol esters, *Celastrus paniculata* extract, Cellulose acetate, Spherical, Ceramide 33 (liquid soy extract), Cetyl triethylammonium dimethicone copolyol phthalate, Chia (*Salvia hispanica*) oil, Chinese hibiscus (*Hibiscus rosa-sinensis*) extract, Chitin, Chitosan, Chitosan glycolate, Chitosan PCA, Cholesteric esters, Cholesterol, Cholesterol isostearate, Cholesteryl/behenyl/octyldodecyllauroyl glutamate, Cholesteryloctyldodecyllauroyl glutamate, Cinchona succirubra extract, Cocodimonium hydroxypropyl hydrolyzed collagen, Cocodimonium hydroxypropyl hydrolyzed silk, Cocodimonium hydroxypropyl hydrolyzed wheat protein, Cocodimonium hydroxypropyl silk amino acids Collagen, Collagen amino acids, Collagen phthalate, Copper acetyl tyrosinate methylsilanol, Copper aspartate, Copper PCA, Copper protein complex, Corn (*Zea mays*) oil, Cottonseed (*Gossypium hirsutum*) oil, Cucumber (*Cucumis sativus*) extract, Cystine hydroxypropyl polysiloxane, Desamido collagen, Dibutyl adipate, Di C12-13 alkyl malate, Dicaprylyl maleate, Diisocetyl dodecanedioate, Diisostearyl adipate, Dimethicone copolyol beeswax, Dimethicone copolyol meadowfoamate, Dimethiconol arginine, Dimethiconol cysteine, Dimethiconol panthenol, Dimethyl hyaluronate, Dimethylsilanol hyaluronate, Dioctyldodecyl climer dilinoleate, Dioctyldodecyl dodecanedioate, Dipentaerythritol fatty acid ester, Dipentaerythrityl hexahydroxystearate, Dipentaerythrityl hexahydroxystearate/stearate/rosinate, Dipentaerythrityl tetrahydroxystearate/isostearate, Dog rose (*Rosa canina*) seed extract, *Echitea glauca* extract, Elastin amino acids, *Emblica officinalis* extract, estolides, Ethoxydiglycol oleate, Ethylhexyl hydroxystearate, Ethyl minkate, *Eugenia jambolana* extract, Evening primrose (*Oenothera biennis*) extract, *Galla sinensis* extract, *Ganoderma lucidum* oil, *Gleditsia sinensis* extract, Gliadin, Glycereth-12, Glyceryl alginate, Glyceryl collagenate, Glyceryl polymethacrylate, Glycolic acid, Glycolipids, Glycosaminoglycans, Glycosphingolipids, *Gnetum amazonicum* extract, Grape (*Vitis vinifera*) seed oil, Hazel (*Corylus avellana*) nut oil, Honey (MeI) extract, Hyaluronic acid, Hybrid safflower (*Carthamus tinctorius*) oil, Hybrid sunflower (*Helianthus annuus*) oil, Hydrogenated castor oil, Hydrogenated coconut oil, Hydrogenated cottonseed oil, Hydrogenated lecithin, Hydrogenated palm kernel oil, Hydrogenated palm oil, Hydrogenated phospholipids, Hydrogenated polydecene, Hydrogenated polyisobutene, Hydrogenated soybean/cottonseed oil, Hydrogenated soybean oil, Hydrogenated vegetable oil, Hydrolyzed adansonia digitata extract, Hydrolyzed carbolipoprotein, Hydrolyzed casein, Hydrolyzed collagen, Hydrolyzed fibronectin, Hydrolyzed glycosaminoglycans, Hydrolyzed keratin, Hydrolyzed milk protein, Hydrolyzed oats, Hydrolyzed pea protein, Hydrolyzed placental protein, Hydrolyzed transgenic collagen, Hydrolyzed rice protein, Hydrolyzed serum protein, Hydrolyzed silk, Hydrolyzed soy protein, Hydrolyzed sweet almond protein, Hydrolyzed wheat protein, Hydroxyethyl chitosan, Inositol, Isodecyl salicylate, Isostearyl hydrolyzed animal protein, Japanese hawthorn (*Crataegus cuneata*) extract, Jojoba butter, Jojoba (*Buxus chinensis*) oil, Jojoba esters, Jujube (*Zizyphus jujuba*) extract, Keratin amino acids, Kiwi (*Actinidia chinensis*) fruit extract, Kiwi (*Actinidia chinensis*) seed oil, Kola (*Cola acuminata*) extract, Kukui (*Aleurites molaccana*) nut oil, Lactamide DGA, Lactamide MEA, Lactamidopropyl trimonium chloride, Lactic acid, L(+) Lactic acid, Lactobacillus/whey ferment, *Lactococcus* hydrolysate, Lactoyl methylsilanol elastinate, Laminaria digitata extract, Lanolin, Lanolin alcohol, Lanolin USP, Lanolin modified USP, Lauryldimonium hydroxypropyl hydrolyzed wheat protein, Lauryldimonium hydroxypropyl wheat amino acids, Lauryl methyl PCA, Lauryl PCA, Lecithin, *Lesquerella fendleri* oil, Liposomes, Locust bean (*Ceratonia siliqua*) gum, Lupine amino acids, Lysine PCA, *Macadamia temifolia* nut oil, Magnesium aspartate, Maltitol, Manganese aspartate, Mango (*Mangifera indica*) seed oil, Mannan, Marine polyaminosaccharide, *Maximilliana regia* extract, Meadowfoam glyceryl quaternium, Meadowfoam (*Limnanthes alba*) seed oil, *Melaleuca hypercifolia* extract, Menthyl PCA, Methylsilanol elastinate, Methylsilanol mannuronate, Milk amino acids, Milk lipid, Mineral oil (*Paraffinum liquidum*), Molybdenum aspartate, *Mouriri apiranga* extract, Natto gum, *Nelumbium speciosum* extract, Neopentyl glycol diethylhexanoate, Neopentyl glycol diheptanoate, Octyl hydroxystearate, Octyl stearate, 13-Olefin oligomer, Olive (*Olea europaea*) oil, *Ophiopogon japonicus* extract, Orange (*Citrus aurantium dulcis*) extract, Orange (*Citrus aurantium dulcis*) peel wax, Palm (*Elaeis guineensis*) oil, Palmetto extract, Palm glycerides, Palm kernel glycerides, Pantethine, Panthenol, Panthenyl ethyl ether, Paraffin, Partially hydrogenated soybean oil, Passionflower (*Passiflora incarnata*) oil, Passionfruit seed oil, Peanut (*Arachis hypogaea*) oil, Pea (*Pi sum sativum*) extract, Pecan (*Carya illinoensis*) oil, PEG-4, PEG-6, PEG-8, PEG-12, PEG-8 beeswax, PEG-6 capric glycerides, PEG-6 caprylic/capric glycerides, PEG-70 mango glycerides, PEG-75 shea butter glycerides, PEG-75 shorea butter glycerides, PEG-100 stearate, Pentaerythrityl adipate/caprate/caprylate/heptanoate, Pentaerythrityl isostearate/caprate/caprylate/adipate, Pentaerythrityl stearate/caprate/caprylate/adipate, Pentaerythrityl tetracaprylate/tetracaprate, Pentaerythrityl tetraoleate, Pentylene glycol, Perfluoronyl hydroxyethoxy octyldodecyl meadowfoamate, Perfluoropolymethylisopropyl ether, Petrolatum, Petroleum wax, *Pfaffia* spp. Extract, Phosphatidylcholine, Phospholipids, Phytantriol, Phytosterol, Phytosteryl/octyldodecyllauroyl glutamate, Pistachio (*Pistacia vera*) nut oil, Placental protein, Plankton extract, Polyacrylamidopropyl trimonium chloride, Polyamino sugar condensate, Polybutene, Polyquaternium-7, Polyquatemium-22, Polyquatemium-39, Polyquaternium-47, Polyunsaturated fatty acids, Potassium DNA, Potassium lactate, Potassium PCA, PPG-20 methyl glucose ether distearate PPG-8/SMDI copolymer, Propylene glycol dicaprylate/dicaprate, Propylene glycol dioctanoate, Pumpkin (*Cucurbita pepo*) seed oil, PVP/hydrolyzed wheat protein copolymer, Quinoa (*Chenopodium quinoa*) extract, Rapeseed (*Brassica campestris*) oil, *Rehmannia chinensis* extract, Rice Bran Oil, Rice (*Oryza sativa*) bran oil, Rose water, Royal jelly extract, Saccharide isomerate, *Saccharomyces* lysate extract, *Saccharomyces*/soy protein ferment, Safflower (*Carthamus tinctorius*) oil, Sclerotium gum, Selenium aspartate, Selenium protein complex, Sericin, Serum albumin, Sesame amino acids, Sesame (*Sesamum indicum*) oil, Shea butter (*Butyrospermum parkii*), Shea butter (*Butyrospermum parkii*) extract, Shea butter (*Butyrospermum parkii*) fruit, Shea butter (*Butyrospermum parkii*) oil, Shea butter (*Butyrospermum parkii*) unsaponifiables, Shorea stenoptera butter, Silicone quaternium-13, Silk amino acids, Silkworm lipids, Sodium albumin, Sodium chondroitin sulfate, Sodium DNA, Sodium hyaluronate, Sodium lactate, Sodium PCA, Sodium Polyaspartate, Soluble collagen, Soluble transgenic elastin, Soy amino acids, Soybean (*Glycine soja*) oil, Spirulina amino acids, *Spondias amara* extract, Squalane, Squalene, Stearalkonium dimethicone copolyol phthalate, Steardimonium hydroxypropyl hydrolyzed wheat protein, Stomach extract, Sunflower (*Helianthus annuus*) seed oil, Superoxide dismutase, Sweet almond (*Prunus amygdalus dulcis*) extract, Sweet almond (*Prunus amygdalus dulcis*) oil, Tamarindus indica seed polysaccharide, Tissue extract, Tocopheryl acetate, Tocopheryllinoleate, Tomato (*Solanum lycopersicum*) extract, Tormentil (*Potentilla erecta*) extract, Trehalose, Triundecanoin, Vegetable oil, Walnut (*Juglans regia*) oil, Watercress (*Nasturtium officinale*) extract, Wheat amino acids, Wheat (*Triticum vulgare*) germ extract, Wheat (*Triticum vulgare*) germ oil, Yarrow (*Achillea mille folium*) extract, Yeast beta glucan, Yeast (*Saccharomyces cerevisiae*) extract (Faex), Yogurt filtrate, Yogurt Powder, Zinc acetylmethionate, Zinc aspartate, Zinc PCA and mixtures thereof Particularly preferred particles having emolliency properties may be formed of the emollient compositions disclosed in U.S. Pat. No. RE38,141E, U.S. Pat. No. 5,968,530 and U.S. Pat. No. 6,432,421.

Preferably, at least some of the particles contain one or more antimicrobial agents e.g. antibacterial or antiviral agents. In this way, the composition may deliver one or more of a number of different active antimicrobial agents directly to the surface of the skin via the suspended particles, without being partially volatilized by the evaporating alcohol. Choice of antimicrobial active can be made visually apparent to the user based on the size and colour of the particle. Such antimicrobial agent may be utilized and substituted at will to give efficacy against bacteria, virus, fungus/yeast and spores. The antimicrobial agent may also be used against methicillin resistant *Staphylococcus aureus* (MRSA), vancomycin resistant enterococci (VRE), and other *Staphylococcus aureus* virulent pathogens that may show resistance to commonly used antibiotics.

Suitable antimicrobial agents include Allicin, Benzalkonium chloride, Benzethonium chloride, Benzoic acid, Benzyl alcohol, Bromochlorophene 2-Bromo-2-nitropropane-1,3-diol, Butylparaben, Caprylolyl collagen amino acids, Caprylolyl glycine, Caprylolyl keratin amino acids, Captan, Cetethyldimonium bromide, Cetyl pyridinium chloride, Chlorothymol, Chloroxylenol, Citral, Citron oil, Copper PCA, Dichlorobenzyl alcohol, Dilauryldimonium chloride, Domiphen bromide, Ethylparaben, *Eucalyptus globulus* extract, Fennel (*Foeniculum vulgare*) extract, Garlic (*Allium sativum*) extract, Gentian violet, Glyceryl caprylate, Glyceryllaurate, Hexamidine diisothionate, Hexetidine, Hinokitiol, Honeysuckle (*Lonicera caprifolium*) extract, Honeysuckle (*Lonicera japonica*) extract, *Leptospermum scoparium* oil, Lichen (*Usnea barbata*) extract, Methylparaben, Myristalkonium chloride, Pentylene glycol, *Pfaffia paniculata* extract, Phenethyl alcohol, Phenol, Phenoxyethanol, Phenoxyisopropanol, Phenyl mercuric acetate, Phenyl mercuric benzoate, Phenyl mercuric borate, o-Phenylphenol, Phytosphingosine, Piroctone olamine, Polymethoxy bicyclic oxazolidine, Potassium sorbate, Propylparaben, Ricinoleamodopropyltrimonium ethosulfate, Sage (*Salvia officinalis*) extract, Sodium benzoate, Sodium pyrithione, Sodium ricinoleate, Sodium shale oil sulfonate, Tea tree (*Melaleuca alternifolia*) oil, Thimerosal, Thyme (*Thymus vulgaris*) extract, Thymol, Triclocarban, Triclosan, Undecylenamidopropyltrimonium methosulfate, Undecylenic acid, Zinc oxide, Zinc PCA, Zinc pyrithione, Zinc undecylenate, Aluminum PCA, Ammonium iodide, Butylglucoside caprate, Caprylic/capric glycerides, Chlorhexidine, Chlorhexidine diacetate, Chlorhexidine digluconate, Chlorhexidine dihydrochloride, Chlorphenesin, alpha-Glucan-oligosaccharide, Iceland moss (*Cetraria islandica*) extract, Lactoferrin, Lauralkonium bromide, Lauralkonium chloride, Laurtrimonium chloride, Laurylpyridinium chloride, *Leptospermum scoparium* oil, Mushroom (*Cordyceps sabolifera*) extract, Orange (*Citrus aurantium dulcis*) peel extract, Orange (*Citrus sinensis*) flower extract, PEG-42 ebiriko ceramides extract, Peppermint (*Mentha piperita*) extract, Philodendron (*Phellodendron amurense*) extract, Pine (*Pinus sylvestris*) needle extract, Polymethoxy bicyclic oxazolidine, Quaternium 73, *Rubus thunbergii* extract, Sodium shale oil sulfonate, Sodium usnate, Undecylenic acid, docosanol, eicosanol and mixtures thereof.

The antimicrobial, antibacterial or antiviral agents may be present in the composition in an amount from 0.001 to 10% by weight e.g. from 0.01 to 5% by weight, preferably from 0.01 to 1% by weight and more preferably from 0.05 to 1% by weight.

Unlike conventional AHS that work only until the alcohol dries, the composition of the invention provides extra and residual antimicrobial efficacy via the delivery particles. It is preferred to choose agents to which microbes will not develop resistance. Agents can also be chosen which have reduced propensity to induce allergic response and skin toxicity. Studies have shown that traditional alcohol rubs are ineffective in eliminating *bacillus atrophaeus* (surrogate for anthrax) and spores from hands. Unlike the existing AHS, the composition of the invention is effective against bacterial spores, as it could contain agents such as chlorhexidine gluconate, which are delivered via the suspended particles.

The composition of the invention can offer hospital management speed and flexibility of targeting a critical microbe, whether it is bacterial, viral, fungal or spores, without having to change the equipment, procedures, training or previously purchased sanitizing agent. The composition of the invention can be tailor-made to suit the hospital needs. For example, if there occurred a sudden outbreak of a bacterial infection such as MRSA, a relevant antimicrobial counter-agent, such as allicin, could be added in the form of particles to existing stocks of AHS at the critical site to combat the outbreak. The simplicity and ease of this process means that it does not disrupt operations at unaffected sites and results in the expeditious containment of the contagion.

The composition of the invention may augment other containment strategies, such as isolation. Isolating patients with severe infections (e.g. MRSA) is a long-standing and effective method for preventing the spread of the contagion. Isolation areas are, however, available in finite amount, and once exhausted, isolation ceases to be a tool of containment. Isolation is effective as a normal daily containment strategy, but becomes ineffective during an outbreak that exhausts the hospital's capacity to isolate afflicted patients. The composition of the invention may assist the hospital in avoiding this critical threshold by reducing the amount of cross-contamination and thus reducing the numbers of afflicted people who require isolation. Also enforcement of hand hygiene standards will increase the efficacy of isolation.

The composition of the invention may contain a fragrance and in a preferred embodiment the fragrance is contained in at least some of the particles.

A fragrance may be added to the alcohol/water gel to mask any unpleasant odour of the alcohol or residual antimicrobial agent. As a particular fragrance will not suit everyone's personal preference, some people even preferring a neutral formulation, an advantage of the composition of the invention is that HCW have the opportunity to choose what fragrance they desire, if any. The required particles can be simply added to the base alcohol sanitizer gel if and when necessary. A composition containing a fragrance may also provide proof of use. HCW supervisors are able to enforce proper hand hygiene standards if they can smell whether or not HCW are using the composition.

The fragrance may be present in the composition in an amount from 0.01 to 2% by weight.

In a further embodiment of the invention, the composition may contain a marker activated by ultra violet radiation (a UV marker) and in a preferred embodiment the UV marker is contained in at least some of the particles. Use of a UV marker enables HCW supervisors to easily enforce that HCW are indeed using the composition and that they are adhering to proper hand hygiene standards. UV markers that glow under a UV light source will be left on the hands after handwashing. The 'hand glow test' can confirm that the HCW have indeed complied with handwashing regulations. It would be more difficult for the HCW to defeat this test than to simply comply with standards.

A pH buffer or neutralizing agent may also be present in the composition to create a formulation that is closer to the pH of skin. This ingredient is not a critical addition. However, an alcohol/water formulation whose pH has been modified, will be less damaging to the skin and thus the user will be less inclined to reduce usage. Neutralizing agents, such as, diisopropanolamine, triethanolamine, potassium hydroxide and sodium or a pH buffer such as lactate/lactic acid, may be used to modify the acidity and alkalinity of the alcohol/water fluid. The concentration of neutralizing agent added to this AHS is best described by the pH range required. The pH range may vary from 4 to 8, preferably from 4 to 7, more preferably from 5 to 6.

If desired, the composition may also contain a chelating agent, for example EDTA however this may not be necessary if ultra pure water and alcohol are used in manufacture. The quantity of chelating agent used may be within the range of 0-1%, preferably about 0.01% by weight.

It is advantageous for at least some of the particles to contain a colouring agent. In this way, it is possible to visually recognize which active ingredients are present in a specific composition based on the appearance of the suspended particles. This assists visual quality control at every level, enables the user to recognise if the composition contains the particles necessary to carry out its critical purpose, and indeed if the correct ingredients have been provided. Similarly, if any user has an allergy to a specific ingredient, an alternative formulation may be offered which is visually different and acceptable. If the user is readily equipped with the knowledge of the contents of the composition, the user can be assured that the composition is less harmful to the skin and that it contains the relevant active ingredients to be effective. The peace of mind gained from the acquired knowledge of the content of a particular composition, facilitates the enforcement of proper hand hygiene standards.

In a preferred embodiment of the invention the composition comprises a set of particles having a particular composition and at least one other set of particles having a different composition. For example, the composition may comprise a set of particles containing an emollient and another set of particles containing one or more antimicrobial, antibacterial or antiviral agents. Advantageously, each set of particles is coloured to distinguish it from each other set of particles. The colour may identify the type of particle or a specific ingredient in the particle.

In a further preferred embodiment, the composition of the set of particles containing an emollient and/or moisturizer has a penetration as measured in accordance with ASTM D 1321-92 that is lower than that of the composition of the set of particles containing one or more antimicrobial agents.

In another preferred embodiment, the particles containing an emollient and/or moisturizer are larger than the particles containing one or more antimicrobial agents.

In this way, the secondary antimicrobial ingredient is activated first and spread by further rubbing as the harder particles are abraded.

The particles may be prepared in a variety of ways. For example, the material from which the particles or beads are to be made may be heated to render it liquid. The liquid is then pumped through an injection needle into a cold bath in which the particles formed are insoluble. Alternatively, instead of injecting drops of the warm liquid into the cold bath, the warm solution may be dripped from above onto the surface of a cold immiscible liquid. A particularly efficient process comprises mechanically dispersing the warm solution in a cold immiscible liquid using an agitator. The rate or degree of agitation determines the size of the beads produced.

The composition of the invention is very convenient to use. The composition may be used without any additional water and towels. The preparation may be packaged in small personal bottles, or in wall-mounted dispenser units in strategic locations, for example at the foot of a patient's bed. There is no need to invest in new facilities to use the proposed composition. Units require minimal maintenance and may be easily relocated without using skilled labour.

The composition may be created by simply mixing together the correct quantities of alcohol, water and thickener (as disclosed above) and possibly an activating agent to create a substantially thick liquid or gel of the desired viscosity (viscosity range is disclosed above). At least one type of particle is then added to the thick liquid/gel and stirred to create a formulation in which the suspended particles are distributed substantially evenly. The particles may contain any one or more of the ingredients from the list comprising emollients, moisturisers, antimicrobial agents, neutralizing agents, chelating agents, colours, fragrances and UV markers. The concentrations of all the components and the type of additional components can be varied to change the properties in order to suit the needs of the health care environment at the time of production.

The present invention facilitates enforcement of proper hand hygiene standards by incorporating particles within the alcohol/water fluid. The composition can be designed to be more compatible with HCW needs, more effective, aesthetically pleasing, and non-skin dehydrating. Changes can be readily made to the composition that makes it more convenient and attractive to the HCW. This flexibility encourages regular use of the composition. As described above, various active ingredients can be provided within the particles. The particles can be modified to combat bacteria, viruses, fungus/yeast and possibly spores, specific to the requirements of the health care environment at the time. If the sanitizer incorporates an antibacterial agent within the particles, then the present invention is a more effective sanitizer than conventional AHS because the antimicrobial agents leave a residue active agent on the skin after washing. Preferably, the particles are coloured and can be distinguished visually; therefore it is possible to identify the ingredients and check the compatibility of the composition with the HCW and the health care environment. The suspended particles can be felt by the HCW during use. They wear away and preferably spread and absorb into skin only after a standard and controllable amount of rubbing energy has been expended. For this reason, a HCW is compelled to give the alcohol gel a more thorough and complete application than a conventional AHS. A fragrance or UV-activated particles could also be incorporated within the AHS. This could allow the HCW supervisor to check whether the HCW is adhering to the hand sanitation regulations using a by smell or shining UV radiation onto hands.

For the reasons noted above, use of the composition of the invention with suspended particles will result in a more effective handwashing routine, thus enforcing handwashing standards.

The invention is further illustrated by way of example as follows.

Compositions in accordance with the invention were prepared. For each composition, mixing the components shown produced an alcohol gel. Two different types of particle were added to the alcohol gel of each composition and stirred therein to form a uniform suspension of particles in the gel. In the following Examples, Phase A refers to the gel or "continuous phase" while Phase B refers to the suspended particles. All percentages are by weight unless otherwise specified.

Example 1

| Nr. | Component | Composition | % |
|---|---|---|---|
| A | | Continuous Phase | |
| 1. | Alcohol | Ethyl Alcohol | 62.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS) with Triclosan | 0.8 |
| | | TOTAL: | 100.0 |

Fluorescent Brightener 236 is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone Example 2

| Nr. | Component | Composition | % |
|---|---|---|---|
| A | | Continuous Phase | |
| 1. | Alcohol | Isopropyl Alcohol | 62.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS Green) with Triclosan | 0.8 |
| | | TOTAL: | 100.0 |

Example 3

| Nr. | Component | Composition | % |
|---|---|---|---|
| A | | Continuous Phase | |
| 1. | Alcohol | Ethyl Alcohol | 62.0 |
| 2. | Water | Deionised Water | Q.S. |
| 3. | Thickener | Carbomer (Carbopol Ultrez 10) | 0.3 |
| 3a. | Neutralizer | Triethanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Antibacterial | Agar spheres with allicin (garlic extract) | 0.8 |
| | | TOTAL: | 100.0 |

Example 4

| Nr. | Component | Composition | % |
|---|---|---|---|
| A | | Continuous Phase | |
| 1. | Alcohol | Isobutanol and Ethanol 1:1 | 65.0 |
| 2. | Water | Deionised Water | Q.S. |
| 3. | Thickener | Xanthan Gum | 1.0 |
| 3a. | Neutralizer | Triethanolamine | 0.1 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS) with Gentian Violet | 0.8 |
| | | TOTAL: | 100.0 |

Gentian Violet particles will be purple. Xanthan Gum (thickener) does not always require a neutralizer.

Example 5

| Nr. | Component | Composition | % |
|---|---|---|---|
| A | | Continuous Phase | |
| 1. | Alcohol | Ethyl Alcohol | 62.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Antibacterial | Agar spheres with Ethylparaben, Butylparaben and Propylparaben | 0.8 |
| | | TOTAL: | 100.0 |

Example 6

| Nr. | Component | Composition | % |
|---|---|---|---|
| A | | Continuous Phase | |
| 1. | Alcohol | n-propanol | 62.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Antibacterial | Agar spheres with Phenoxyisopropanol | 0.8 |
| | | TOTAL: | 100.0 |

Example 7

| Nr. | Component | Composition | % |
|---|---|---|---|
| A | | Continuous Phase | |
| 1. | Alcohol | Isobutanol | 65.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Sodium Hydroxide | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS) with Chlorhexidine digluconate | 0.8 |
| | | TOTAL: | 100.0 |

Example 8

| Nr. | Component | Composition | % |
|---|---|---|---|
| A | | Continuous Phase | |
| 1. | Alcohol | Benzyl Alcohol | 70.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS Orange) with Orange Peel Extract | 0.8 |
| | | TOTAL: | 100.0 |

Example 9

| Nr. | Component | Composition | % |
|---|---|---|---|
| A | | Continuous Phase | |
| 1. | Alcohol | n-butanol | 65.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | (Florasomes MXS) with Copper PCA, Aluminium PCA and Zinc PCA | 0.8 |
| | | TOTAL: | 100.0 |

Example 10

| Nr. | Component | Composition | % |
|---|---|---|---|
| A | | Continuous Phase | |
| 1. | Alcohol | Ethyl Alcohol and Benzyl Alcohol | 70.0 |
| 2. | Water | Deionised Water | Q.S. |
| 3. | Thickener | Acrylates/C10–30 Alkyl Acrylate Crosspolymer (Carbopol ETD 2020) | 0.3 |
| 3a. | Neutralizer | Diisopropanolamine | 0.1 |
| 3b. | Chelant | Disodium EDTA | 0.01 |
| B | | Suspended Particles | |
| 4. | Moisturizer, Fragrance and UV Marker | (Florasomes MXS Blue) with Fragrance and Fluorescent Brightener 236 | 0.5 |
| 5. | Moisturizer and Antibacterial | Agar spheres with Chlorphenesin | 0.8 |
| | | TOTAL: | 100.0 |

The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

The invention claimed is:

1. A sanitizing composition comprising:
a viscous liquid comprising alcohol, water, and a thickener; and
a plurality of essentially homogeneous particles comprising:
a particle-forming material; and
an antimicrobial agent different than the alcohol in the viscous liquid;
wherein the alcohol is present in a range between about 55% to about 80% by weight; and wherein the plurality of particles are adapted to abrade away completely when rubbed.

2. The sanitizing composition of claim 1, wherein at least some of the plurality of particles additionally comprise an additional component selected from the group consisting of an emollient, a moisturizer, an ultraviolet (UV) marker and combinations thereof.

3. The sanitizing composition of claim 1, wherein the antimicrobial agent different than the alcohol in the viscous liquid is selected from the group consisting of:
Allicin, Benzalkonium chloride, bacteriophages, Benzethonium chloride, Benzoic acid, Benzyl alcohol, Bromochlorophene 2-Bromo-2-nitropropane-1,3-diol, Butylparaben, Caprylolyl collagen amino acids, Capryloyl glycine, Capryloyl keratin amino acids, Captan, Cetethyldimonium bromide, Cetyl pyridinium chloride, Chlorothymol, Chloroxylenol, Citral, Citron oil, Copper PCA, Dichlorobenzyl alcohol, Dilauryldimonium chloride, Domiphen bromide, Ethylparaben, *Eucalyptus globulus* extract, Fennel (*Foeniculum vulgare*) extract, Garlic (*Allium sativum*) extract, Gentian violet Glyceryl caprylate, Glyceryllaurate, Hexamidine diisothionate, Hexetidine, Hinokitiol, Honeysuckle (*Lonicera caprifolium*) extract, Honeysuckle (*Lonicera japonica*) extract, *Leptospermum scoparium* oil, Lichen (*Usnea barbata*) extract, Methylparaben, Myristalkonium chloride, Pentylene glycol, *Pfaffia paniculata* extract, Phenethyl alcohol, Phenol, Phenoxyethanol, Phenoxyisopropanol, Phenyl mercuric acetate, Phenyl mercuric benzoate, Phenyl mercuric borate, o-Phenylphenol, Phytosphingosine, Piroctone olamine, Polymethoxy bicyclic oxazolidine, Potassium sorbate, Propylparaben, Ricinoleamodopropyltrimonium ethosulfate, Sage (*Salvia officinalis*) extract, Sodium benzoate, Sodium pyrithione, Sodium ricinoleate, Sodium shale oil sulfonate, Tea tree (*Melaleuca alternifolia*) oil, Thimerosal, Thyme (*Thymus vulgaris*) extract, Thymol, Triclocarban, Triclosan, Undecylenamidopropyltrimonium methosulfate, Undecylenic acid, Zinc oxide, Zinc PCA, Zinc pyrithione, Zinc undecylenate, Aluminum PCA, Ammonium iodide, Butylglucoside caprate, Caprylic/capric glycerides, Chlorhexidine, Chlorhexidine diacetate, Chlorhexidine digluconate, Chlorhexidine dihydrochloride, Chlorphenesin, alpha-Glucan-oligosaccharide, Iceland moss (*Cetraria islandica*) extract, Lactoferrin, Lauralkonium bromide, Lauralkonium chloride, Laurtrimonium chloride, Laurylpyridinium chloride, *Leptospermum scoparium* oil, Mushroom (*Cordyceps sabolifera*) extract, Orange (*Citrus aurantium dulcis*) peel extract, Orange (*Citrus sinensis*) flower extract, PEG-42 ebiriko ceramides extract, Peppermint (*Mentha piperita*) extract, Philodendron (*Phellodendron amurense*) extract, Pine (*Pinus sylvestris*) needle extract, Polymethoxy bicyclic oxazolidine, Quaternium 73, *Rubus thunbergii* extract, Sodium shale oil sulfonate, Sodium usnate, Undecylenic acid, Zinc PCA, docosanol, eicosanol and mixtures thereof.

4. The composition of claim 3, wherein the thickener is selected the group consisting of:
Acrylates/C10-C30 alkyl acrylate crosspolymer, Acrylates/ceteth-20 itaconate copolymer, Acrylates/ceteth-20 methacrylates copolymer, Acrylates/palmeth-25 acrylate copolymer, Acrylates/steareth-20 itaconate copolymer, Acrylates/steareth-20 methacrylate copolymer, Acrylates/steareth-50 acrylate copolymer, AcrylatesNA crosspolymer, Acrylates/vinyl isodecanoate crosspolymer, Acrylic acid/acrylonitrogens copolymer, Algin, Aluminum/magnesium hydroxide stearate, Ammonium acrylates/acrylonitrogens copolymer, Ammonium alginate, Ammonium polyacryl dimethyl tauramide/VA, Arachidyl alcohol, Attapulgite, Behenic acid, Behenyl alcohol, Behenyl behenate, Bentonite, CI-5 alkyl galactomannan CIS-36 acid, CIS-36 acid glycol ester, CIS-36 acid triglyceride, Calcium alginate, Calcium carrageenan, C12-15 alcohols, C12-16 alcohols, Caprylic alcohol, Carbomer, Carboxymethyl hydroxyethylcellulose, Carrageenan (*Chondrus crispus*), Cellulose, Cellulose gum, Ceteareth-3, Ceteareth-60 myristyl glycol, Cetearyl alcohol, Cetearyl behenate, Cetearyl octanoate, Cetearyl stearate, Cetostearyl stearate, Cetyl alcohol, Cetyl betaine, Cetyl esters, Cetyl hydroxyethylcellulose, Cetyl myristate, Cetyl palmitate, Cocamide, Cocamide DEA, Cocamide MEA, Cocamide MIPA, Cocamidopropylamine oxide, Cocamidopropyl betaine, Coco-betaine, Coco/oleamidopropyl betaine, Coco-rapeseedate, Cocoyl amido hydroxy sulfobetaine, Cocoyl monoethanolamide ethoxylate, Colloidal silica sols, DEA-hydrolyzed lecithin DEA-linoleate, DEA-oleth-3 phosphate, DEA oleth-10 phosphate, Decyl alcohol, Dextran, Dextrin, Dihydroxyethyl Tallowamime, Dioleate, Dilaureth-10 phosphate, Dilinoleamidopropyl dimethyl amine, Dioleth-S phosphate, DMHF, Ethoxylated fatty alcohol, Ethylcellulose, Gellan gum, Glucouis, Glyceryl behenate, Glyceryl poly methacrylate, Glyceryl stearate, Glyceryl stearate SE, Guar (*Cyanopsis tetragonoloba*) gum, Guar hydroxypropyltrimonium chloride, Hectorite, Hexyl alcohol, Hydrated silica, Hydrogenated rapeseed oil, Hydrogenated starch hydrolysate, Hydrogenated vegetable glycerides, Hydrolyzed oat flour, Hydrolyzed transgenic collagen, Hydroxyethylcellulose, Hydroxypropylcellulose, Hydroxypropyl chitosan, Hydroxypropyl guar, Hydroxypropyl methylcellulose, Isoceteth-10, Isostearamide DEA, Isostearamidopropylamine oxide, Jojoba wax, Karaya (*Stericulia urens*) gum, Lauramide DEA, Lauramidopropyl betaine, Laureth-3, Laureth-10, Lauric acid, Lauric-linoleic DEA, Lauroyl-linoleoyl diethanolamide, Lauroyl-myristoyl diethanolamide, Lauryl alcohol, Lauryl betaine, Linoleamide DEA, Linoleic acid, Linolenic acid, Lithium magnesium sodium silicate, Locust bean (*Ceratonia siliqua*) gum, Mannan gum, Magnesium aluminum silicate, MDM hydantoin, Methylcellulose, Montmorillonite, Myristamide DEA, Myristamide MEA, Myristamine oxide, Myristic acid, Myristyl alcohol, Octacosanyl stearate, Oleamide, Oleamide DEA, Palmitamide MEA, Paraffin, Pectin, PEG-8, PEG-80 Glyceryl tallowate, PEG-8 PPG-3 Diisostearate, PEG-200 Hydrogenated glyceryl palmate, PEG-5M, PEG-9M, PEG-23M, PEG-45M, PEG-90M, PEG-160M, PEG-6 beeswax, PEG-S beeswax, PEG-12 beeswax, PEG-150/decyl/SMDI copolymer, PEG-4 diisostearate, PEG-8 dioleate, PEG-3 distearate, PEG-4 distearate, PEG-8 distearate, PEG-150 distearate, PEG-18 glyceryl oleatelcocoate, PEG-200 glyceryl stearate, PEG-28 glyceryl tallowate, PEG-200 glyceryl tallowate, PEG-7 hydrogenated castor oil, PEG-40 jojoba oil, PEG-3 lauramide, PEG-3 laura mine oxide, PEG-2 laurate, PEG-120 methyl glucose dioleate, PEG-4 oleamide, PEG-ISO pentaerythrityl tetrastearate, PEG-55 propylene glycol oleate, PEG-4 rapeseedamine, PEG-160 sorbitan triisostearate, PEG-S stearate, PEG-75 stearate, PEG-100 stearate, PEG-150/stearyl/SMDI copolymer, PEG-50 tallow amide, Pentaerythrityl tetrabehenate, Pentaerythrityl tetrastearate, Poloxamer 105, Poloxamer 124, Poloxamer 185, Poloxamer 237, Poloxamer 238, Poloxamer 338, Poloxamer 407, Polyacrylic acid, Polyquaternium-37, Polysorbate 20, Potassium alginate, Potassium chloride, Potassium oleate, Potassium stearate, PPG-5-ceteth-10 phosphate, PPG-14 laureth-60 alkyl dicarbamate, PPG-14 palmeth-60 alkyl dicarbamate, Propylene glycol stearate, Propylene glycol stearate SE, PVMIMA decadiene crosspolymer, PVP, Quaternium-90, Bentonite, Quaternium-18 bentonite, Quaternium-18 hectorite, Rapeseed oil, ethoxylated high erucic acid, Ricinoleamide MEA, Sclerotium gum, Sesamide, DEA, Silica, Sodium acrylates/vinyl isodecanoate crosspolymer, Sodium carbomer, Sodium carrageenan, Sodium ceteth-13-carboxylate, Sodium chloride, Sodium hyaluronate, Sodium hydroxypropyl starch phosphate, Sodium isostearoamphopropionate, Sodium lauryl sulfoacetate, Sodium magnesium silicate, Sodium stearate, Sorbitan sesquiisostearate, Sorbitan tristearate, Soy amide DEA, Soyamidopropyl betaine, Starch polyacrylonitrile copolymer-potassium salt, Starch polyacrylonitrile copolymer-sodium salt, Stearalkonium bentonite, Stearalkonium hectorite, Stearamide, Stearamide, DEA, Stearamide MEA, Stearamide MEA-stearate, Stearamidopropyl dimethyl amine lactate, Stearamine oxide, Steareth-10 alkyl ether/acrylates copolymer, Stearic acid, Stearyl alcohol, Synthetic beeswax, Tallowamide MEA, TEA-acrylates/acrylonitrogens copolymer, Tragacanth (*Astragalus gummifer*) gum, Tribehenin, Trideceth-2 carboxamide MEA, Trihydroxystearin, Tromethamine magnesium aluminum silicate, Wheat germamide DEA, Wheat germamidopropyl betaine, Xanthan gum, and mixtures thereof.

5. The composition of claim 4, wherein the particle forming material is selected from the group consisting of jojoba esters, collagen, natural polymers and synthetic polymers and mixtures thereof.

6. The composition of claim 5, wherein the plurality of particles have a hardness of between about 80 and about 160 measured according to ASTM D 1321-92 at 25° C. and a diameter of between about 250 μm to 1500 μm.

7. The composition of claim 1, wherein the particles additionally comprise a UV marker, and the UV marker is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

8. The composition of claim 5, wherein the particles comprise a UV marker, and the UV marker is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

9. The composition of claim 2, wherein the particles comprise a UV marker, and the UV marker is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

10. The composition of claim 1, wherein the particle forming material is selected from the group consisting of jojoba esters, collagen, and synthetic polymers and mixtures thereof.

11. The sanitizing composition of claim 10, wherein the antimicrobial agent different than the alcohol in the viscous liquid is selected from the group consisting of:

Allicin, Benzalkonium chloride, bacteriophages, Benzethonium chloride, Benzoic acid, Benzyl alcohol, Bromochlorophene 2-Bromo-2-nitropropane-1,3-diol, Butylparaben, Capryloyl collagen amino acids, Capryloyl glycine, Capryloyl keratin amino acids, Captan, Cetethyldimonium bromide, Cetyl pyridinium chloride, Chlorothymol, Chloroxylenol, Citral, Citron oil, Copper PCA, Dichlorobenzyl alcohol, Dilauryldimonium chloride, Domiphen bromide, Ethylparaben, *Eucalyptus globulus* extract, Fennel (*Foeniculum vulgare*) extract, Garlic (*Allium sativum*) extract, Gentian violet Glyceryl caprylate, Glyceryllaurate, Hexamidine diisothionate, Hexetidine, Hinokitiol, Honeysuckle (*Lonicera caprifolium*) extract, Honeysuckle (*Lonicera japonica*) extract, *Leptospermum scoparium* oil, Lichen (*Usnea barbata*) extract, Methylparaben, Myristalkonium chloride, Pentylene glycol, *Pfaffia paniculata* extract, Phenethyl alcohol, Phenol, Phenoxyethanol, Phenoxyisopropanol, Phenyl mercuric acetate, Phenyl mercuric benzoate, Phenyl mercuric borate, o-Phenylphenol, Phytosphingosine, Piroctone olamine, Polymethoxy bicyclic oxazolidine, Potassium sorbate, Propylparaben, Ricinoleamodopropyltrimonium ethosulfate, Sage (*Salvia officinalis*) extract, Sodium benzoate, Sodium pyrithione, Sodium ricinoleate, Sodium shale oil sulfonate, Tea tree (*Melaleuca alternifolia*) oil, Thimerosal, Thyme (*Thymus vulgaris*) extract, Thymol, Triclocarban, Triclosan, Undecylenamidopropyltrimonium methosulfate, Undecylenic acid, Zinc oxide, Zinc PCA, Zinc pyrithione, Zinc undecylenate, Aluminum PCA, Ammonium iodide, Butylglucoside caprate, Caprylic/capric glycerides, Chlorhexidine, Chlorhexidine diacetate, Chlorhexidine digluconate, Chlorhexidine dihydrochloride, Chlorphenesin, alpha-Glucan-oligosaccharide, Iceland moss (*Cetraria islandica*) extract, Lactoferrin, Lauralkonium bromide, Lauralkonium chloride, Laurtrimonium chloride, Laurylpyridinium chloride, *Leptospermum scoparium* oil, Mushroom (*Cordyceps sabolifera*) extract, Orange (*Citrus aurantium dulcis*) peel extract, Orange (*Citrus sinensis*) flower extract, PEG-42 ebiriko ceramides extract, Peppermint (*Mentha piperita*) extract, Philodendron (*Phellodendron amurense*) extract, Pine (*Pinus sylvestris*) needle extract, Polymethoxy bicyclic oxazolidine, Quaternium 73, *Rubus thunbergii* extract, Sodium shale oil sulfonate, Sodium usnate, Undecylenic acid, Zinc PCA, docosanol, eicosanol and mixtures thereof.

12. The composition of claim 10, wherein the particles comprise a UV marker, and the UV marker is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

13. A method of preparing a sanitizing composition, the method comprising:

providing a viscous liquid or gel comprising about 55% to about 80% by weight alcohol, water and a thickener; and adding a plurality of essentially homogeneous particles to the viscous liquid or gel, wherein the plurality of essentially homogeneous particles comprise a particle-forming material and an antimicrobial agent different than the alcohol in the viscous liquid; and wherein the plurality of particles are adapted to abrade away completely when rubbed.

14. The method of claim 13, wherein at least some of the plurality of particles additionally comprise at least one of an emollient, a moisturizer, and an ultraviolet (UV) marker.

15. The method of claim 13, wherein at least some of the plurality of particles additionally comprise 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

16. The method of claim 13, wherein the particle forming material is selected from the group consisting of jojoba esters, collagen, natural polymers and synthetic polymers and mixtures thereof.

17. A sanitizing composition comprising:
a viscous liquid comprising alcohol, water, and a thickener; and
a plurality of essentially homogeneous particles comprising an ultraviolet (UV) marker; wherein the alcohol is present in a range between about 30% to about 95% by weight; and wherein the plurality of particles are adapted to abrade away completely when rubbed.

18. The sanitizing composition of claim 17, wherein the plurality of particles comprises a material selected from the group consisting of jojoba esters, collagen, natural polymers and synthetic polymers and mixtures thereof; and wherein the UV marker is 2H-1-Benzopyran-2-one, 7-(2H-Naphtho[1,2-d]Triazol-2-yl)-3-Phenyl-7-(2H-Naphtho[1,2-d]Triazol-2-yl)-3-Phenyl-2-Benzopyrone.

* * * * *